(12) United States Patent
Hsu et al.

(10) Patent No.: US 10,232,126 B2
(45) Date of Patent: Mar. 19, 2019

(54) DISPOSABLE PRE-FILLED SYRINGE

(71) Applicants: Pei-Hsin Hsu, Taichung (TW); Pei-Yang Hsu, Taichung (TW); Wei-Ni Hsu, Taichung (TW)

(72) Inventors: Pei-Hsin Hsu, Taichung (TW); Pei-Yang Hsu, Taichung (TW); Wei-Ni Hsu, Taichung (TW)

( * ) Notice: Subject to any disclaimer, the term of this patent is extended or adjusted under 35 U.S.C. 154(b) by 183 days.

(21) Appl. No.: 15/284,857

(22) Filed: Oct. 4, 2016

(65) Prior Publication Data
US 2017/0021109 A1 Jan. 26, 2017

Related U.S. Application Data

(63) Continuation-in-part of application No. 14/064,530, filed on Oct. 28, 2013.

(30) Foreign Application Priority Data

Jan. 9, 2013 (TW) .............................. 102100689 A

(51) Int. Cl.
*A61M 5/32* (2006.01)
*A61M 5/24* (2006.01)

(52) U.S. Cl.
CPC .......... *A61M 5/321* (2013.01); *A61M 5/2455* (2013.01); *A61M 5/2466* (2013.01); *A61M 5/3202* (2013.01); *A61M 2005/2407* (2013.01)

(58) Field of Classification Search
CPC .. A61M 5/321; A61M 5/2455; A61M 5/3202; A61M 5/2466; A61M 2005/2407
See application file for complete search history.

(56) References Cited

U.S. PATENT DOCUMENTS

| | | | | | |
|---|---|---|---|---|---|
| 1,712,070 | A | * | 5/1929 | Cressler | A61M 5/24 285/376 |
| 2,737,949 | A | * | 3/1956 | Brown | A61M 5/24 604/192 |
| 6,027,472 | A | * | 2/2000 | Kriesel | A61M 5/14526 604/232 |
| 2003/0073958 | A1 | * | 4/2003 | Pond | A61M 5/24 604/232 |
| 2003/0109831 | A1 | * | 6/2003 | Ito | A61M 5/5066 604/187 |

* cited by examiner

*Primary Examiner* — Amber R Stiles
(74) *Attorney, Agent, or Firm* — C. G. Mersereau; DeWitt LLP

(57) ABSTRACT

A disposable pre-filled syringe has a protecting tube, a medication filling tube, a separating plug, a pushing module, and a needle module. The medication filling tube is made of chemically inert material and is mounted in the protecting tube. The separating plug is mounted in an end of the medication filling tube. The pushing module is slidably inserted into the medication filling tube opposite to the separating plug. The needle module is mounted on an end of the protecting tube.

13 Claims, 9 Drawing Sheets

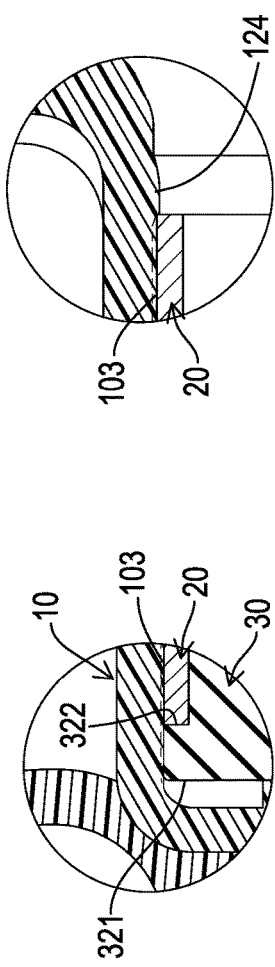
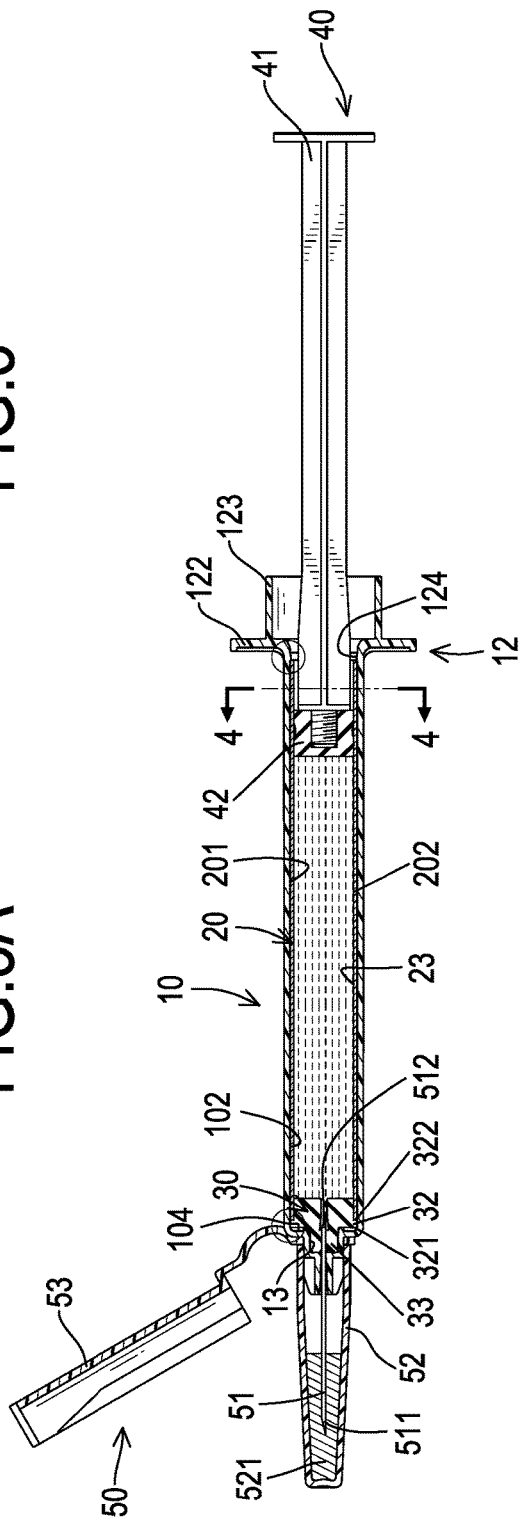
FIG.3
FIG.3A
FIG.2

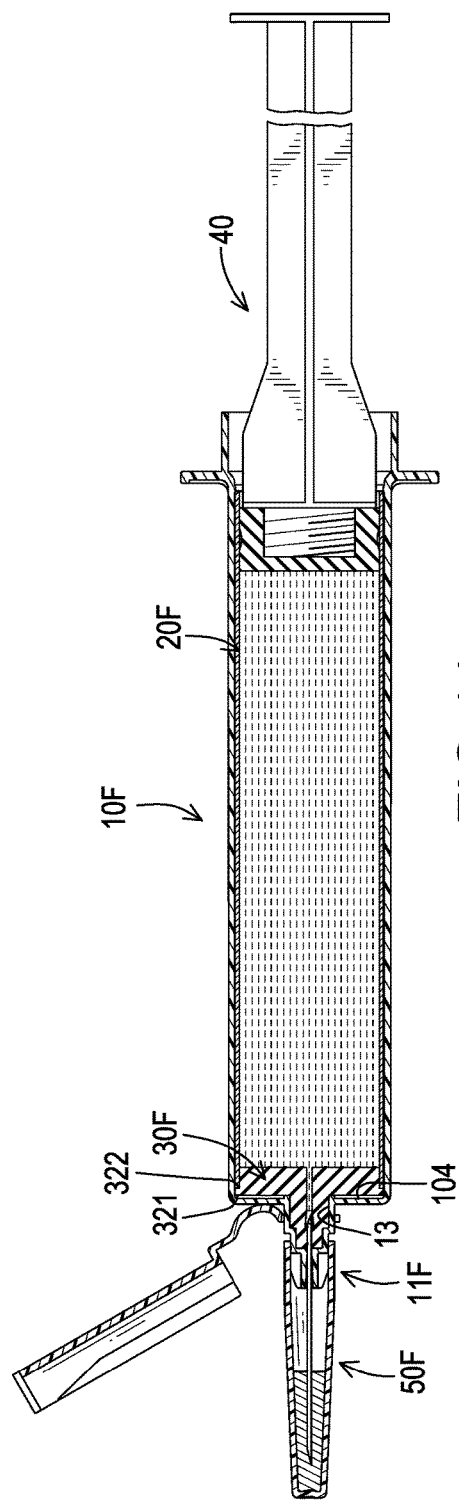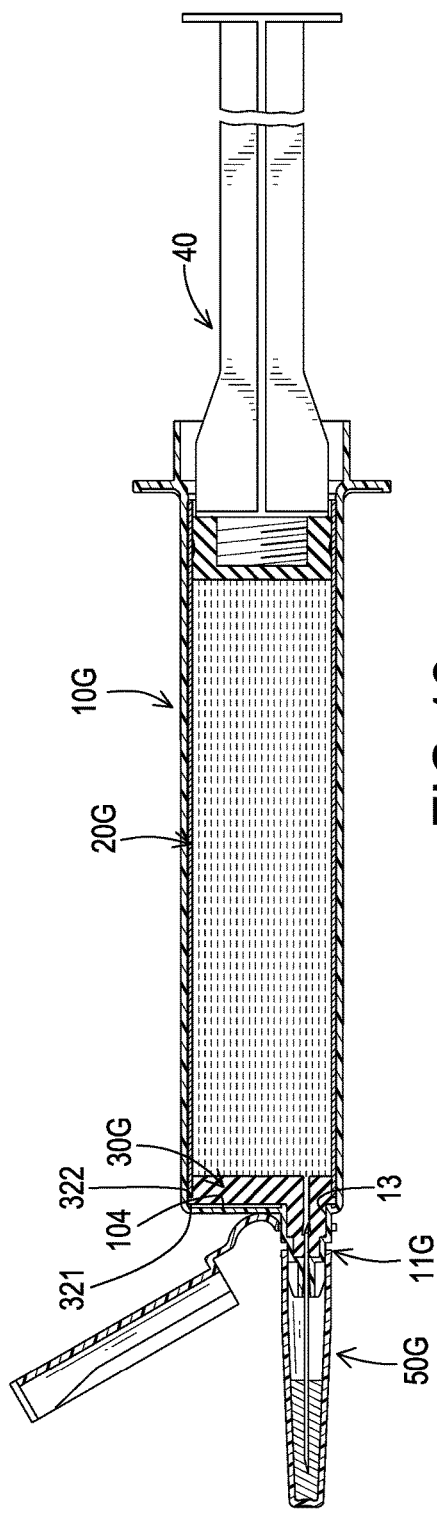

DISPOSABLE PRE-FILLED SYRINGE

The present invention is a continuation-in-part of U.S. patent application Ser. No. 14/064,530, filed on Oct. 28, 2013. This application claims the priority benefit of Taiwan patent application number 102100689 filed on Jan. 9, 2013.

BACKGROUND OF THE INVENTION

1. Field of the Invention

The present invention relates to a disposable syringe, and more particularly to a disposable pre-filled syringe.

2. Description of Related Art

A conventional disposable syringe is made by plastic injection molding, such that the conventional disposable syringe is low-cost and for single use only. After a disposable syringe is used, the syringe has to be disposed of or discarded properly to prevent infections among healthcare workers.

Prior to use, the conventional disposable syringe is filled with medication which is prepared from a preserved bottle or vial. Such a handling process is complicated and may produce many medical wastes. On the other hand, the conventional plastic disposable syringe is not suitable for use as a pre-filled syringe since the plastic ingredients and additives may spontaneously leach into, and/or be extracted out by the pre-filled medication, specifically when referring to the biopharmaceuticals. Moreover, some currently available disposable pre-filled syringes are used to store high value medications, such as vaccines or drugs for treating chronic diseases, and are made of special thermoformed polymer or glass materials. As such, the costs of those conventional disposable pre-filled syringes are high, and the manufacturing processes of those syringes are complicated and energy-consuming.

SUMMARY OF THE INVENTION

The main objective of the present invention is to provide a disposable pre-filled syringe to resolve the aforementioned problems.

The disposable pre-filled syringe comprises a protecting tube, a medication filling tube, a separating plug, a pushing module, and a needle module.

The protecting tube is made of plastic and comprises an axis, an outside wall, an inside wall, multiple elongated ribs, a holding portion, a needle mounting portion, a tube space, and an abutting portion. The outside wall is annularly formed along the axis of the protecting tube and is located at an exterior of the protecting tube. The inside wall is annularly formed along the axis of the protecting tube and is located at an interior of the protecting tube. The holding portion comprises an insertion hole formed through the holding portion. The needle mounting portion is opposite to the holding portion. The tube space is formed in surrounding by the inside wall in the protecting tube along the axis of the protecting tube and communicates with the insertion hole and the needle mounting portion. The abutting portion is mounted radially on the inside wall and is adjacent to the needle mounting portion. The multiple elongated ribs longitudinally protrude from the inside wall along the axis of the protecting tube at a length of as long as the tube space, and the elongated ribs are arranged at equal spacing intervals on the inside wall.

The medication filling tube is transparent and made of chemically inert material such as glass, is mounted in the tube space and comprises an axis, an inner diameter and an interior wall surface, an outer diameter and an exterior wall surface, a medication storage space, a pushing module entrance, and a plug hole. The axis of the medication filling tube is parallel with the axis of the protecting tube. The inner diameter is uniform along the axis of the medication filling tube. The outer diameter is also uniform along the axis of the medication filling tube. The length of the medication filling tube is slightly less than a length of each one of the elongated ribs of the protecting tube. The medication storage space is formed interiorly in the medication filling tube surrounded by the interior wall surface along the axis of the medication filling tube. The exterior wall surface of the medication filling tube abuts the elongated ribs of the protecting tube. The pushing module entrance is formed through an end of the medication filling tube and communicates with the medication storage space. The plug hole is formed through an end of the medication filling tube opposite to the pushing module entrance and communicates with the medication storage space.

The separating plug is mounted into the plug hole and abuts against the terminal end of the medication filling tube on one side and concomitantly abuts against the abutting portion of the protecting tube on the opposite side. The pushing module is slidably and hermetically mounted in the medication filling tube and comprises a pushing stick and a pushing plug. The pushing stick is mounted into the medication storage space through the pushing module entrance and has a combining portion. The pushing plug is removably mounted on the combining portion of the pushing stick and slidably and hermetically mounted in the medication storage space. The needle module is mounted on the needle mounting portion.

Other objectives, advantages and novel features of the present invention will become more apparent from the following detailed description when taken in conjunction with the accompanying drawings.

BRIEF DESCRIPTION OF THE DRAWINGS

FIG. 2 is a side view in partial section of the disposable pre-filled syringe in FIG. 1;

FIG. 3 is an enlarged side view showing the engaging edge of the disposable pre-filled syringe in FIG. 2;

FIG. 3A is an enlarged side view showing the abutting portion of the disposable pre-filled syringe in FIG. 2;

FIG. 11 is an operational side view in partial section of a second preferred embodiment of the disposable pre-filled syringe of the present invention; and FIG. 12 is an operational side view in partial section of a third preferred embodiment of the disposable pre-filled syringe of the present invention.

DETAILED DESCRIPTION OF PREFERRED EMBODIMENT

Figure 1:
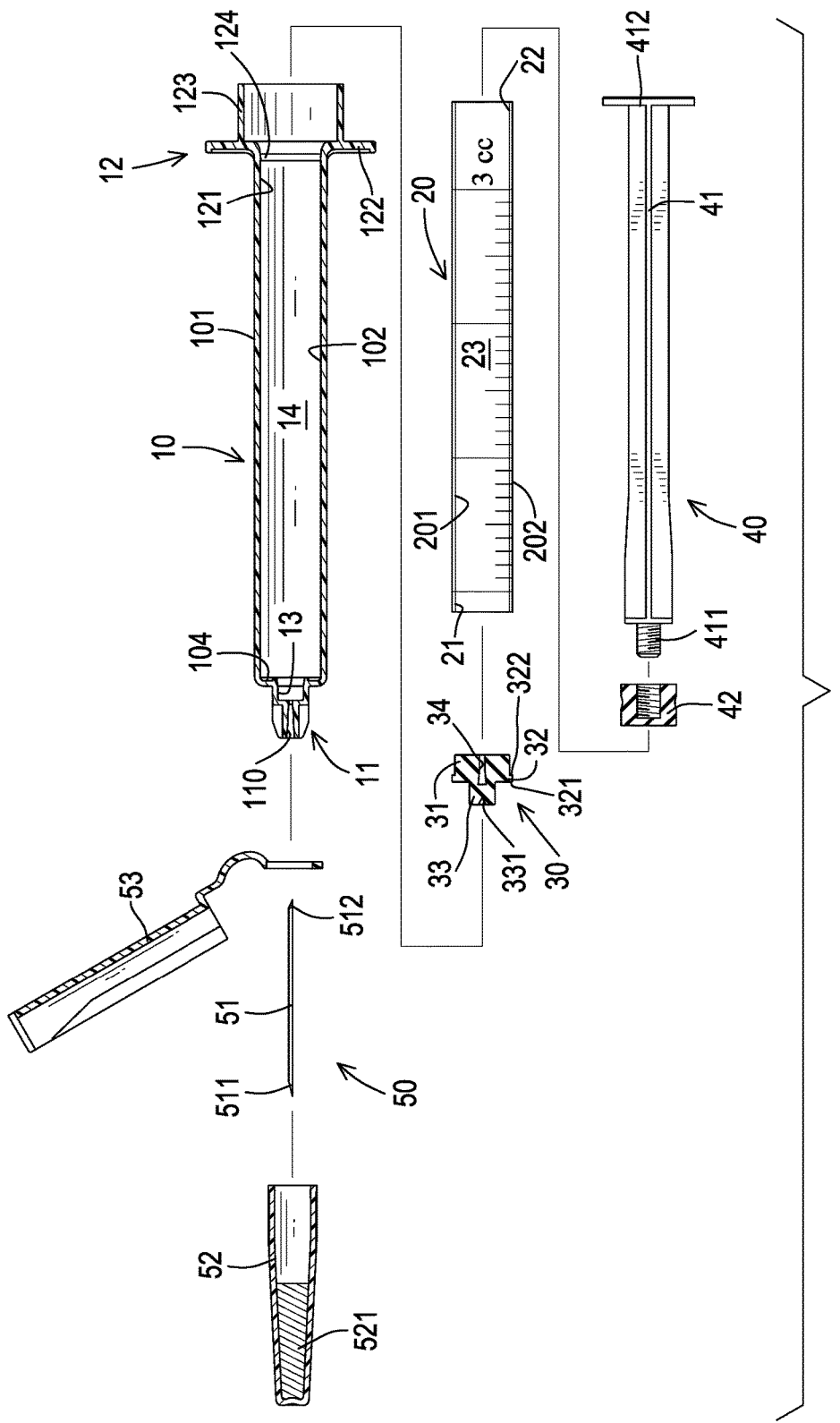
FIG. 1 is an exploded side view in partial section of a first preferred embodiment of a disposable pre-filled syringe in accordance with the present invention.

With reference to FIGS. 1 to 5, a first preferred embodiment of a disposable pre-filled syringe in accordance with the present invention comprises a protecting tube 10, a medication filling tube 20, a separating plug 30, a pushing module 40, and a needle module 50.

Figure 4:
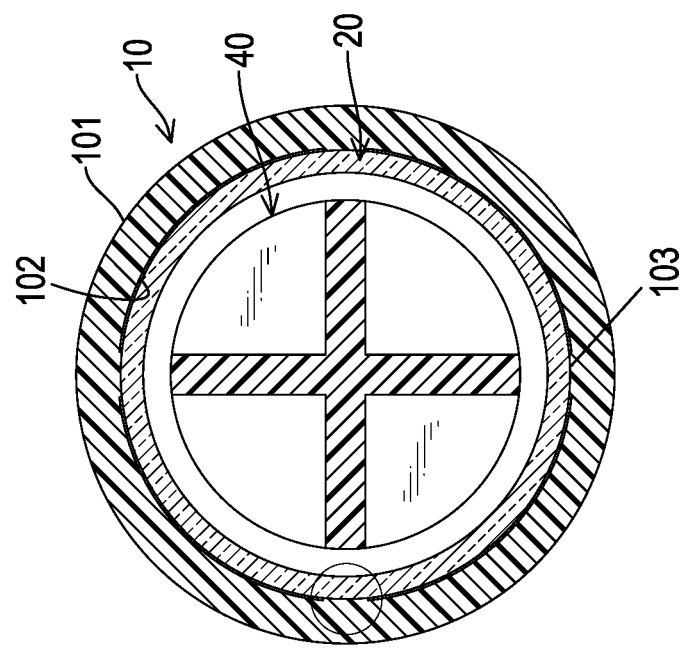
FIG. 4 is a cross sectional side view of the disposable pre-filled syringe along line 4-4 in FIG. 2.
Figure 5:
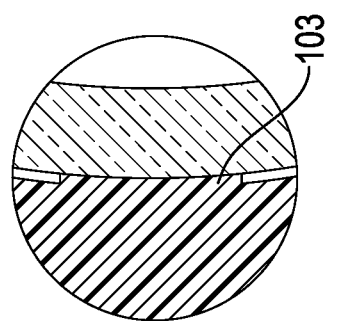
FIG. 5 is an enlarged side view of the disposable pre-filled syringe in FIG. 4.
Figure 6:
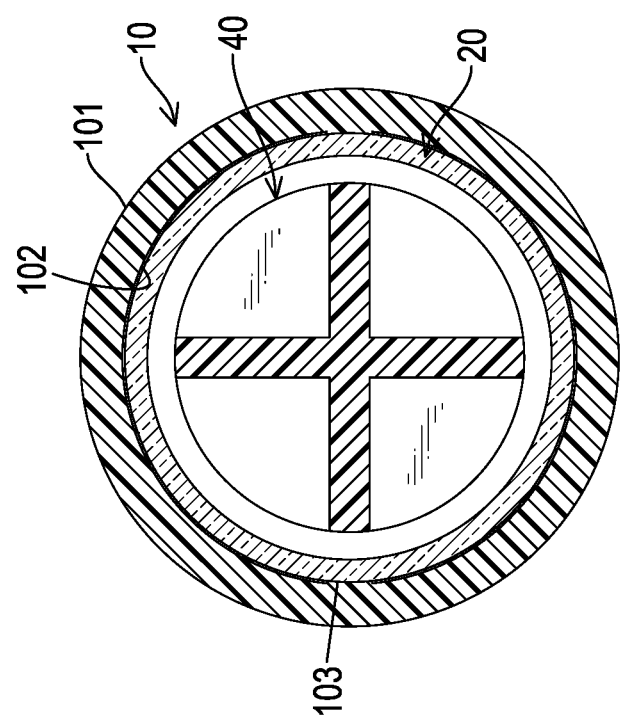
FIG. 6 is a cross sectional side view of a disposable pre-filled syringe in another embodiment of the present invention.
Figure 7:
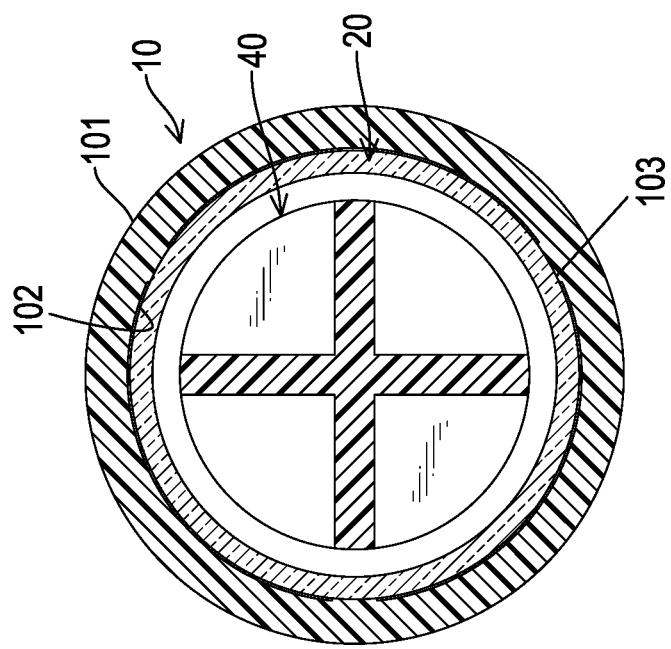
FIG. 7 is a cross sectional side view of a disposable pre-filled syringe in still another embodiment of the present invention.
Figure 8:
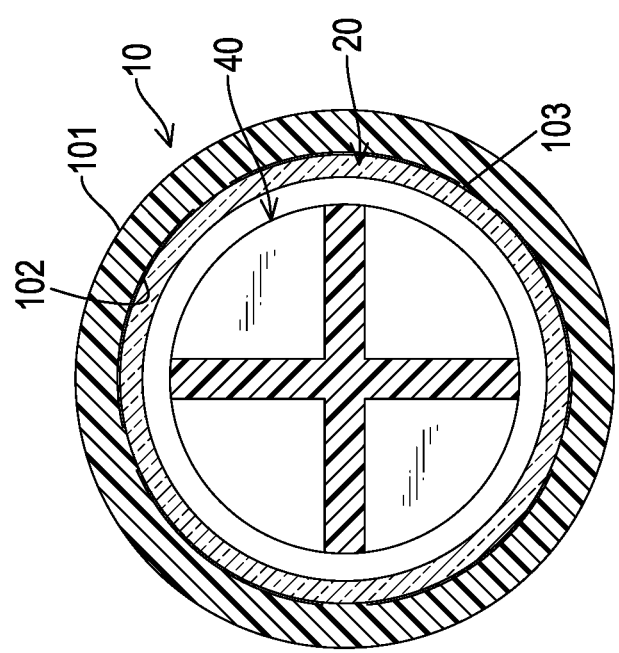
FIG. 8 is a cross sectional side view of a disposable pre-filled syringe in further another embodiment of the present invention.
Figure 9:
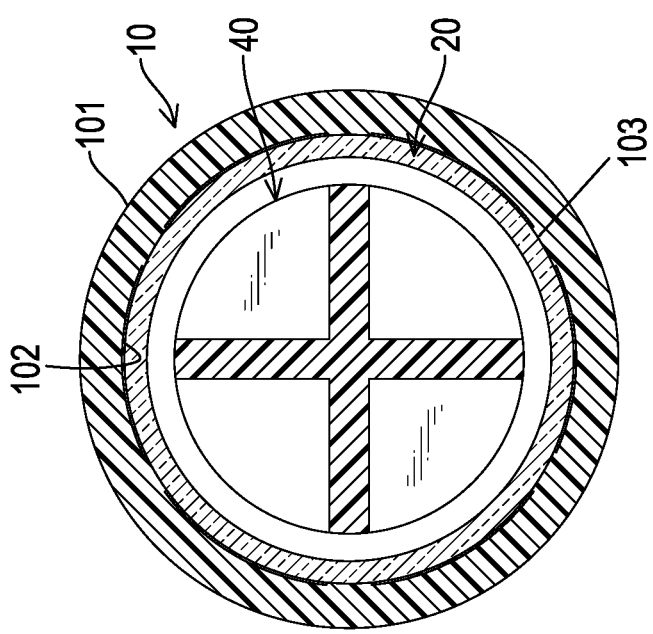
FIG. 9 is a cross sectional side view of a disposable pre-filled syringe in still further another embodiment of the present invention.

The protecting tube 10 may be made of semi-rigid materials such as plastic, and the protecting tube 10 comprises an axis, an outside wall 101, an inside wall 102, a tube space 14, multiple elongated ribs 103, an abutting portion 104, a holding portion 12, a trough 13, and a needle mounting portion 11. The outside wall 101 and the inside wall 102 are annularly formed along the axis of the protecting tube 10 and are located respectively at an exterior and an interior of the protecting tube 10. With reference to FIGS. 4 and 5, the elongated ribs 103 longitudinally protrude from the inside wall 102 along the axis of the protecting tube 10. The elongated ribs 103 being an integral part of the protecting tube 10 are also made of plastic materials and characterized with semi-rigid and flexibility. The elongated ribs 103 are arranged at equal spacing intervals on the inside wall 102. Especially with reference to FIGS. 4 and 5, a number of the elongated ribs 103 is four. The four elongated ribs 103 are arranged at equal spacing intervals on the inside wall 102 with each interval on the inside wall 102 being a quarter circle. In other embodiments, with reference to FIG. 6, a number of the elongated ribs 103 is two. With reference to FIG. 7, a number of the elongated ribs 103 is three. With reference to FIG. 8, a number of the elongated ribs 103 is five. With reference to FIG. 9, a number of the elongated ribs 103 is six.

With reference to FIGS. 1 and 2, the abutting portion 104 is mounted radially on the inside wall 102 and is adjacent to a front end of the inside wall 102. The tube space 14 is formed in surrounding by the inside wall 102 in the protecting tube 10 along the axis of the protecting tube 10. The holding portion 12 is formed at a rear end of the protecting tube 10 and comprises an insertion hole 121, a holding flange 122, an annular piece 123, and an engaging edge 124. The insertion hole 121 is formed through the holding portion 12 and communicates with the tube space 14. The holding flange 122 radially and partial-annularly protrudes from an exterior of the holding portion 12. The annular piece 123 is mounted on a rear side of the holding flange 122. The engaging edge 124 circumferentially protrudes from an interior of the holding portion 12 and is adjacent to the insertion hole 121. The trough 13 is tubular, is connected with the abutting portion 104, is located at a front end of the protecting tube 10 and communicates with the tube space 14. The needle mounting portion 11 abuts the front end of the inside wall 102. The needle mounting portion 11 comprises a needle mounting hole 110 formed through the needle mounting portion 11 along the axis of the protecting tube 10 and communicating with the tube space 14.

With reference to FIGS. 1 and 2, the medication filling tube 20 is used to be filled with and store the medication. The medication filling tube 20 can be mounted into and fixed in the tube space 14 as an integrated part of the protecting tube 10 and is engaged by the elongated ribs 103. The medication filling tube 20 may be made of transparent and thermoplastic material, such as glass or cyclic olefin polymers, which is chemically inert and scientifically regard as hardly releases unstable ingredients or additives from the materials into the pre-filled medication. The medication filling tube 20 comprises an axis parallel with the axis of the protecting tube 10, an inner wall surface 201 of uniform inner diameter, an external wall surface 202 of uniform outer diameter, a medication storage space 23 surrounded by the inner wall surface 201, a pushing module entrance 22, and a plug hole 21. The inner diameter is uniform along the axis of the medication filling tube 20. The outer diameter is also uniform along the axis of the medication filling tube 20. The pushing module entrance 22 and the plug hole 21 are formed through two opposite ends of the medication filling tube 20 respectively and communicate with the medication storage space 23. The pushing module entrance 22 aligns with the insertion hole 121. The plug hole 21 aligns with the trough 13. The external wall surface 202 of the medication filling tube 20 abuts the elongated ribs 103 of the protecting tube 10. With reference to FIGS. 3 and 3A, a length of the medication filling tube 20 is slightly less than a length of each elongated ribs 103. The medication filling tube 20 abuts against the engaging edge 124 with one end and abuts intermediately cushioned by an elastomer on the abutting portion 104 with the opposite end respectively, such that the position of the medication filling tube 20 relative to the protecting tube 10 is fixed by the engaging edge 124 and the abutting portion 104.

With reference to FIGS. 1 and 2, the separating plug 30 is mounted in the plug hole 21 and the trough 13 on opposite directions. The separating plug 30 is made of chemically inert thermoplastic elastomer. The separating plug 30 comprises a plug body 31, a peripheral block flange 32, a protrusion 33, a puncture slit 331, and a leading hole 34. The plug body 31 is mounted in the plug hole 21 hermetically. The peripheral block flange 32 is peripherally and annularly formed around the plug body 31, is adjacent to the front end of the plug body 31 and abuts against the abutting portion 104 at a front side 321, such that the peripheral block flange 32 is used as a washer for the medication filling tube 20 with that the end of the medication filling tube 20 adjacent to the plug hole 21 abuts on the abutting portion 104 is intermediately cushioned by the peripheral block flange 32 by engaging a rear side 322 of the peripheral block flange 32. The protrusion 33 is formed on and protrudes from a front end of the plug body 31 and is mounted in the trough 13. The puncture slit 331 is formed medially on the protrusion 33. The leading hole 34 is formed centrally in the plug body 31 with an axis in accordance with the axis of the protecting tube 10 and communicates with the medication storage space 23. The puncture slit 331 and the leading hole 34 align with the needle mounting hole 110, and a needle 51 can penetrate through and be fixed in the needle mounting hole 110. The needle can further penetrate the protrusion 33 through the puncture slit 331 into the leading hole 34. Alternatively, the puncture slit 331 is formed medially through the protrusion 33 and in communicating with the leading hole 34 and the medication storage space 23, and in alignment with the needle mounting portion 11. A cap can be mounted in front of the protrusion 33 then cover on the puncture slit 331 selectively. The front end of the puncture slit 331 can be blocked by the cap.

With reference to FIGS. 1 to 3, the pushing module 40 is mounted in the medication storage space 23 of the medication filling tube 20 through the pushing module entrance 22, and can be hermetically pushed or pulled along the axis of the protecting tube 10. The pushing module 40 comprises a pushing stick 41 and a pushing plug 42. The pushing stick 41 is mounted on the pushing plug 42 in the medication storage space 23 through the pushing module entrance 22 and comprises a combining portion 411 and a handle portion 412. The combining portion 411 is mounted on a front end of the pushing stick 41 and is located in the medication storage space 23. The handle portion 412 is mounted on a rear end of the pushing stick 41 opposite the combining portion 411 for facilitating pushing or pulling of the pushing stick 41. The pushing plug 42 may be made of chemically inert thermoplastic elastomer. The pushing plug 42 is removably mounted on the combining portion 411 by threads, and is hermetically slidable in the medication filling tube 20.

Figure 10:
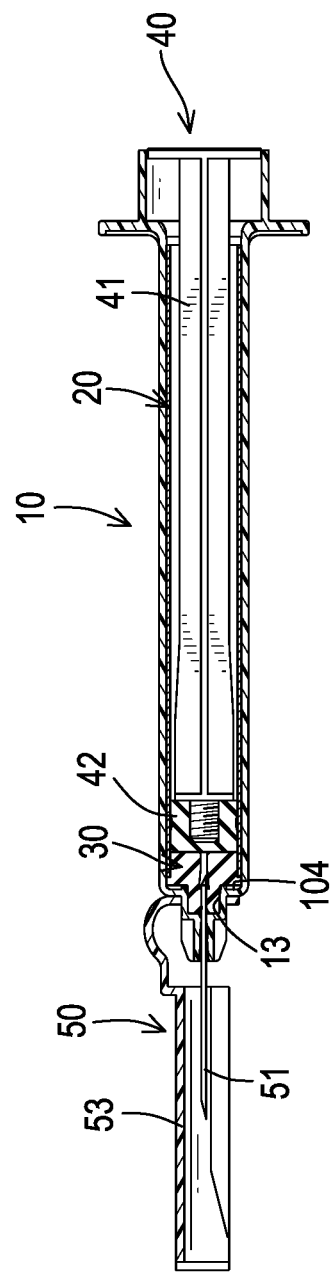
FIG. 10 is an operational side view of the disposable pre-filled syringe in FIG. 1.

With reference to FIGS. 1 to 3, the needle module 50 is mounted on the needle mounting portion 11 and comprises a needle 51, a protecting cover 52, and a safety cover 53. The needle 51 comprises a puncture end 512 and an injection end 511. The puncture end 512 is fixed in the needle mounting hole 110 and penetrates the protrusion 33 through the puncture slit 331 into the leading hole 34, such that the needle 51 can communicate with the leading hole 34 and the medication storage space 23. The protecting cover 52 is mounted around the needle mounting portion 11 and comprises a sealing plug 521 mounted in the protecting cover 52. The sealing plug 521 is made of chemically inert thermoplastic elastomer and is transfixed by the injection end 511. The safety cover 53 is mounted around the protecting tube 10 and is selectively engaged with the needle 51 after injection of the medication, as shown in FIG. 10, to keep the user from inadvertently needle stick by the needle 51.

With reference to FIG. 2, under an unpacked condition, the medication storage space 23 is pre-filled with medication. It is noted that the medication can be stored in the closed medication storage space 23 safely and stably since the medication filling tube 20 is made of stable glass or chemically inert polymers, such as cyclic olefin polymers, and is closed by the chemically inert separating plug 30 and the pushing plug 42. The stable closed medication storage space 23 may eliminate medication toxicological impacts or detrimental immunogenic responses and denaturation of stored medication caused by generally known undesired drug-container interactions, the chemical/physical reactions between the medication ingredients and the leachables and extractables of extremely high temperature thermoplastically formed conventional glass pre-filled syringes that comprises unstable internal molecular structure at the reshaped portion caused by extremely heating-and-reshaping processes that detrimentally disrupted the originally stable intermolecular alignments of the glass tubing ingredients. Moreover, the medication filling tube 20 is protected by the elongated ribs 103 and the surrounding protecting tube 10 of plastic materials. Therefore, the rigid fragile glass medication filling tube 20 may not be damaged easily during transportation. When the medication filling tube 20 is inserted into the tube space 14 of the protecting tube 10, the resistance and the friction may be mitigated from abutment with the elongated ribs 103 thus facilitate assembly of the medication filling tube 20 and the protecting tube 10. The separating plug 30 is transfixed by the punctured end 512 of the needle 51 to guide the medication. The injection end 511 of the needle 51 is sealed by the chemically inert sealing plug 521. When the disposable pre-filled syringe is in use, the protecting cover 52 is removed from the needle 51. The pushing stick 41 is engaged with the pushing plug 42 by threads. The pushing stick 41 is further pushed by the user to push the medication. The medication stored in the medication storage space 23 is exerted with the pressure from the pushing plug 42, and then flows through the needle 51 for injection performance. With reference to FIG. 10, after the injection is finished, the safety cover 53 shields the needle 51 to keep the user from inadvertently injured by the needle 51.

The disposable pre-filled syringe not only can simplify the medication preparing process in the clinical practice, but also can reduce medical waste pollution and erroneous dosing in the medication administration as compared with the conventional syringes use. The medication filling tube 20 can store medication on a long term basis to spare the consumption of conventional medication containers. Furthermore, the disposable pre-filled syringe can be adopted for immediate use to increase the efficiency of clinical operation.

With reference to FIG. 11, a second preferred embodiment of the disposable pre-filled syringe in accordance with the present invention comprises a protecting tube 10F, a medication filling tube 20F, a separating plug 30F, a pushing module 40, and a needle module 50F. The capacities of the protecting tube 10F and the medication filling tube 20F may both be featured for the medication amount of about 25 cc in volume. A needle mounting portion 11F of the protecting tube 10F is located at the middle of a front end of the protecting tube 10F.

With reference to FIG. 12, a third preferred embodiment of the disposable pre-filled syringe in accordance with the present invention comprises a protecting tube 10G, a medication filling tube 20G, a separating plug 30G, a pushing module 40, and a needle module 50G. The capacities of the protecting tube 10G and the medication filling tube 20G may both be featured for the medication amount of about 25 cc in volume. A needle mounting portion 11G of the protecting tube 10G is located at a peripheral of a front end of the protecting tube 10G.

Accordingly, the disposable pre-filled syringe uses multiple protecting tubes 10 and multiple medication filling tubes 20 of different sizes to store different volumes of specific medications. The medications are stored in the medication filling tubes 20 safely and stably. The complicated process for clinical medication injection can be simplified efficiently. The risks of medication contamination and erroneous dosing can be reduced. Furthermore, medical waste and discarded containers are also reduced in quantity.

What is claimed is:

1. A disposable pre-filled syringe comprising:
   a protecting tube made of plastic, being semi-rigid and flexible, and comprising
      an axis;
      an outside wall annularly formed along the axis of the protecting tube and located at an exterior of the protecting tube;
      an inside wall annularly formed along the axis of the protecting tube and located at an interior of the protecting tube;
      a holding portion comprising
         an insertion hole formed through the holding portion; and
         an engaging edge circumferentially protruding from an interior of the holding portion and adjacent to the insertion hole;
      a needle mounting portion opposite to the holding portion;
      a tube space formed in and surrounded by the inside wall in the protecting tube along the axis of the protecting tube and communicating with the insertion hole and the needle mounting portion;

multiple elongated ribs being an integral part of the protecting tube, longitudinally protruding from the inside wall along the axis of the protecting tube at a length of as long as the tube space; and an abutting portion mounted radially on the inside wall and adjacent to the needle mounting portion;

a medication filling tube made of glass that is chemically inert material, being transparent, mounted in the tube space, and the medication filling tube and the protecting tube being fixed relative to each other so that the medication filling tube and the protecting tube have no relative movements, wherein an exterior of the medication filling tube abuts the elongated ribs of the interior of the protecting tube, the medication filling tube comprising two opposite ends, wherein one of the ends abuts the engaging edge;

an axis parallel with the axis of the protecting tube;

an inner wall surface of uniform inner diameter along the axis of the medication filling tube;

an external wall surface of uniform outer diameter along the axis of the medication filling tube;

a medication storage space formed interiorly in the medication filling tube surrounded by the inner wall surface along the axis of the medication filling tube;

a pushing module entrance formed through an end of the medication filling tube and communicating with the medication storage space; and a plug hole formed through an end of the medication filling tube opposite to the pushing module entrance and communicating with the medication storage space;

a separating plug being elastic, hermetically mounted into the plug hole and abutting against a terminal end of the medication filling tube on one side and concomitantly abutting against the abutting portion of the protecting tube on the opposite side and having a plug body mounted in the plug hole hermetically, wherein one of the ends of the medication filling tube at a position opposite to the engaging edge is clamped between the protecting tube and the plug body; and a peripheral block flange peripherally and annularly formed around the plug body and abutting between the abutting portion and one of the ends of the medication filling tube at a position opposite to the engaging edge;

a pushing module slidably and hermetically mounted in the medication filling tube and comprising a pushing stick mounted into the medication storage space through the pushing module entrance and having a combining portion; and a pushing plug removably mounted on the combining portion of the pushing stick and slidably and hermetically mounted in the medication storage space; wherein the medication storage space is hermetically closed by the pushing plug and the separating plug; and a needle module mounted on the needle mounting portion.

2. The disposable pre-filled syringe as claimed in claim 1, wherein the holding portion further comprises
a holding flange radially protruding from an exterior of the holding portion; and the protecting tube further comprises a trough connected with the abutting portion, located at a front end of the protecting tube and communicating with the tube space.

3. The disposable pre-filled syringe as claimed in claim 2, wherein the needle mounting portion further comprises a needle mounting hole formed through the needle mounting portion along the axis of the protecting tube.

4. The disposable pre-filled syringe as claimed in claim 2, wherein the separating plug further comprises
a protrusion formed on an end of the separating plug and mounted in the trough.

5. The disposable pre-filled syringe as claimed in claim 2, wherein the separating plug further comprises a leading hole communicating with the medication storage space.

6. The disposable pre-filled syringe as claimed in claim 5, wherein the needle mounting portion of the protecting tube is located at a middle of the front end of the protecting tube.

7. The disposable pre-filled syringe as claimed in claim 5, wherein the needle mounting portion of the protecting tube is located at a periphery of the front end of the protecting tube.

8. The disposable pre-filled syringe as claimed in claim 2, wherein the needle module comprises a needle;
the trough extends through the front end of the protecting tube; and
the separating plug further comprises
a protrusion formed on an end of the separating plug and mounted in the trough; and
a leading hole formed in the separating plug.

9. The disposable pre-filled syringe as claimed in claim 2, wherein the needle module comprises a needle;
the trough extends through the front end of the protecting tube; and
the separating plug further comprises
a protrusion formed on an end of the separating plug and mounted in the trough; and
a leading hole formed through the separating plug.

10. The disposable pre-filled syringe as claimed in claim 9, wherein the needle is fixed in and communicates with the leading hole.

11. The disposable pre-filled syringe as claimed in claim 1, wherein a number of the elongated ribs is two, three, four, five, or six around the inside wall of the protecting tube.

12. The disposable pre-filled syringe as claimed in claim 1, wherein the separating plug further comprises a leading hole communicating with the medication storage space.

13. The disposable pre-filled syringe as claimed in claim 1, wherein the needle module is fixed on the needle mounting portion and comprises a needle which is fixed in the needle mounting portion, piercing through the separating plug and communicating with the medication storage space.

* * * * *